US 8,844,193 B2

(12) United States Patent
Luongo

(10) Patent No.: US 8,844,193 B2
(45) Date of Patent: Sep. 30, 2014

(54) APPARATUS FOR KILLING AND REMOVING TICKS

(76) Inventor: Joseph Luongo, Toms River, NJ (US)

( * ) Notice: Subject to any disclaimer, the term of this patent is extended or adjusted under 35 U.S.C. 154(b) by 461 days.

(21) Appl. No.: 13/277,195

(22) Filed: Oct. 19, 2011

(65) Prior Publication Data

US 2012/0090219 A1 Apr. 19, 2012

Related U.S. Application Data

(60) Provisional application No. 61/394,391, filed on Oct. 19, 2010.

(51) Int. Cl.
*A01M 1/20* (2006.01)
*A01M 3/00* (2006.01)
*A01M 7/00* (2006.01)
*A61B 17/50* (2006.01)
*A61B 17/30* (2006.01)

(52) U.S. Cl.
CPC .............. *A01M 3/00* (2013.01); *A61B 17/50* (2013.01); *A01M 1/2094* (2013.01); *A61B 2017/505* (2013.01); *A61B 17/30* (2013.01)
USPC .......................................... 43/132.1; 43/134

(58) Field of Classification Search
CPC ......... A01M 3/00; A01M 3/007; A01M 1/20; A01M 7/00; A01M 1/2094; A01M 1/00; A01M 1/10
USPC ............... 43/132.1, 133, 134, 124; 294/99.2; 606/133, 210; D28/55
See application file for complete search history.

(56) References Cited

U.S. PATENT DOCUMENTS

| 210,163 | A | * | 11/1878 | Steinmetz | 43/134 |
|---|---|---|---|---|---|
| 528,257 | A | * | 10/1894 | Murray | 294/99.2 |
| 896,338 | A | * | 8/1908 | Tolman | 294/99.2 |
| 909,939 | A | * | 1/1909 | Richmond | 294/99.2 |
| 1,027,079 | A | * | 5/1912 | Shepard | 294/99.2 |
| 1,081,701 | A | * | 12/1913 | Sandmann | 294/99.2 |
| 1,427,044 | A | * | 8/1922 | Wilson | 294/99.2 |
| 1,464,967 | A | * | 8/1923 | Beauregard | 294/99.2 |
| 1,767,553 | A | * | 6/1930 | Rose | 294/99.2 |
| 1,806,441 | A | * | 5/1931 | Bauer et al. | 294/99.2 |
| 2,021,416 | A | * | 11/1935 | Hansen | 294/99.2 |
| 2,376,135 | A | * | 5/1945 | Frasher | 294/99.2 |
| 2,483,985 | A | * | 10/1949 | Sonn | 294/99.2 |
| 2,665,692 | A | * | 1/1954 | Esperance | 294/99.2 |
| 2,733,716 | A | * | 2/1956 | Roberts | 294/99.2 |
| 2,785,984 | A | * | 3/1957 | Kenaga | 514/744 |
| 2,904,602 | A | * | 9/1959 | Ilgenfritz | 570/135 |
| 3,392,727 | A | * | 7/1968 | Hanlon | 294/99.2 |
| 4,192,204 | A | * | 3/1980 | Feldman | 294/99.2 |
| 4,213,460 | A | * | 7/1980 | Weiner | 43/134 |

(Continued)

FOREIGN PATENT DOCUMENTS

| JP | 2004049048 | A | * | 2/2004 | A01M 3/00 |
|---|---|---|---|---|---|
| JP | 2004135527 | A | * | 5/2004 | A01M 7/00 |

*Primary Examiner* — Darren W Ark
(74) *Attorney, Agent, or Firm* — Thien Tran, Esq.; Access Patent Group, LLC

(57) ABSTRACT

An apparatus for killing and removing ticks from the skin of mammals which includes an aerosol canister. An environmentally safe refrigerant HFO-1234yf is carried within the aerosol canister. A mechanism is for dispensing the environmentally safe refrigerant from the aerosol canister directly onto a tick to immobilize and kill the tick. Another mechanism is for safely removing the dead tick from the skin of a mammal.

7 Claims, 1 Drawing Sheet

(56) References Cited

U.S. PATENT DOCUMENTS

| | | | |
|---|---|---|---|
| 4,303,268 A * | 12/1981 | Davidson | 294/99.2 |
| 4,379,168 A | 4/1983 | Dotolo | |
| D272,664 S * | 2/1984 | Jones | D28/55 |
| 4,442,837 A * | 4/1984 | Keatley | 43/134 |
| 4,593,693 A * | 6/1986 | Schenck | 606/210 |
| 4,834,967 A * | 5/1989 | Locicero | 424/45 |
| 4,843,753 A * | 7/1989 | Mace | 294/99.2 |
| 4,888,015 A * | 12/1989 | Domino | 606/210 |
| 4,938,764 A * | 7/1990 | Glaberson | 606/131 |
| 4,950,281 A * | 8/1990 | Kirsch et al. | 294/99.2 |
| 4,976,718 A * | 12/1990 | Daniell | 606/131 |
| 4,979,771 A * | 12/1990 | Childs, III | 43/144 |
| 5,002,323 A * | 3/1991 | Idsund | 294/100 |
| 5,027,549 A * | 7/1991 | Person | 43/134 |
| 5,078,729 A * | 1/1992 | Eichhorn | 606/210 |
| 5,116,347 A * | 5/1992 | Butler | 606/131 |
| D326,803 S * | 6/1992 | Reil | D8/54 |
| 5,137,318 A * | 8/1992 | Lohman | 294/100 |
| 5,147,369 A * | 9/1992 | Wagner | 606/107 |
| 5,179,840 A * | 1/1993 | Worsfold | 43/124 |
| D332,988 S * | 2/1993 | Pacenti | D22/123 |
| D335,166 S * | 4/1993 | Johnston | D22/122 |
| 5,250,046 A * | 10/1993 | Lee | 606/29 |
| 5,276,306 A * | 1/1994 | Huffman | 43/144 |
| 5,282,737 A * | 2/1994 | Ray | 294/99.2 |
| 5,317,041 A * | 5/1994 | Chapman et al. | 514/763 |
| 5,374,274 A * | 12/1994 | Sproviero et al. | 606/131 |
| 5,380,339 A * | 1/1995 | Webster | 606/131 |
| 5,407,243 A * | 4/1995 | Riemann | 294/100 |
| 5,431,665 A * | 7/1995 | Li | 606/211 |
| 5,447,351 A * | 9/1995 | Klunder | 294/99.2 |
| 5,447,511 A * | 9/1995 | Gadd | 606/131 |
| 5,475,941 A * | 12/1995 | Moore | 43/4 |
| 5,554,161 A * | 9/1996 | Thibeault | 606/131 |
| 5,556,563 A * | 9/1996 | von der Heyde et al. | 43/134 |
| 5,595,569 A * | 1/1997 | Hebbard | 606/131 |
| 5,607,434 A * | 3/1997 | Alvino | 606/131 |
| 5,693,069 A * | 12/1997 | Shallman | 606/207 |
| 5,792,148 A * | 8/1998 | Laxvik | 606/131 |
| 5,795,002 A * | 8/1998 | Boron | 294/99.2 |
| 5,843,094 A * | 12/1998 | Saylor | 606/131 |
| 5,876,409 A * | 3/1999 | Heitz | 606/131 |
| 5,914,062 A * | 6/1999 | von der Heyde | 43/134 |
| 5,979,960 A * | 11/1999 | Osmar | 294/99.2 |
| 5,998,762 A * | 12/1999 | von der Heyde | 219/229 |
| 6,100,501 A * | 8/2000 | von der Heyde | 43/134 |
| 6,102,919 A * | 8/2000 | Licata | 606/131 |
| 6,106,041 A * | 8/2000 | Eckhardt | 294/99.2 |
| 6,206,892 B1 * | 3/2001 | Schick | 606/131 |
| D454,981 S * | 3/2002 | Lamagna et al. | D28/55 |
| 6,413,266 B1 * | 7/2002 | Mason | 606/210 |
| D472,675 S * | 4/2003 | Lamagna | D28/55 |
| 6,683,065 B1 * | 1/2004 | Holzer | 514/63 |
| 6,808,717 B1 * | 10/2004 | Bale | 424/405 |
| D507,678 S * | 7/2005 | Lamagna | D28/55 |
| 6,944,986 B1 * | 9/2005 | Gonzalez et al. | 43/4 |
| 7,210,265 B2 * | 5/2007 | Jacobson | 43/136 |
| D569,553 S * | 5/2008 | Cho | D28/55 |
| D571,915 S * | 6/2008 | Poll et al. | D24/143 |
| 7,531,186 B2 | 5/2009 | Boeckh et al. | |
| 7,604,814 B2 * | 10/2009 | Schaffner et al. | 424/405 |
| 7,699,869 B2 * | 4/2010 | Meinhold et al. | 606/210 |
| 7,726,065 B2 * | 6/2010 | Jacobson | 43/136 |
| 8,323,672 B2 * | 12/2012 | Schaffner et al. | 424/405 |
| 8,366,722 B2 * | 2/2013 | Herweijer et al. | 606/131 |
| 8,393,554 B2 * | 3/2013 | Yamamoto et al. | 239/337 |
| 8,596,557 B2 * | 12/2013 | Yamamoto et al. | 239/337 |
| 2007/0092545 A1 * | 4/2007 | Bale | 424/405 |
| 2007/0112379 A1 * | 5/2007 | Vaic | 606/211 |
| 2008/0069785 A1 | 3/2008 | Jones | |
| 2009/0066101 A1 * | 3/2009 | Cho | 294/99.2 |
| 2009/0270354 A1 * | 10/2009 | Schaffner et al. | 514/159 |
| 2010/0227010 A1 | 9/2010 | Jones | |
| 2011/0301617 A1 * | 12/2011 | Bach | 43/132.1 |

* cited by examiner

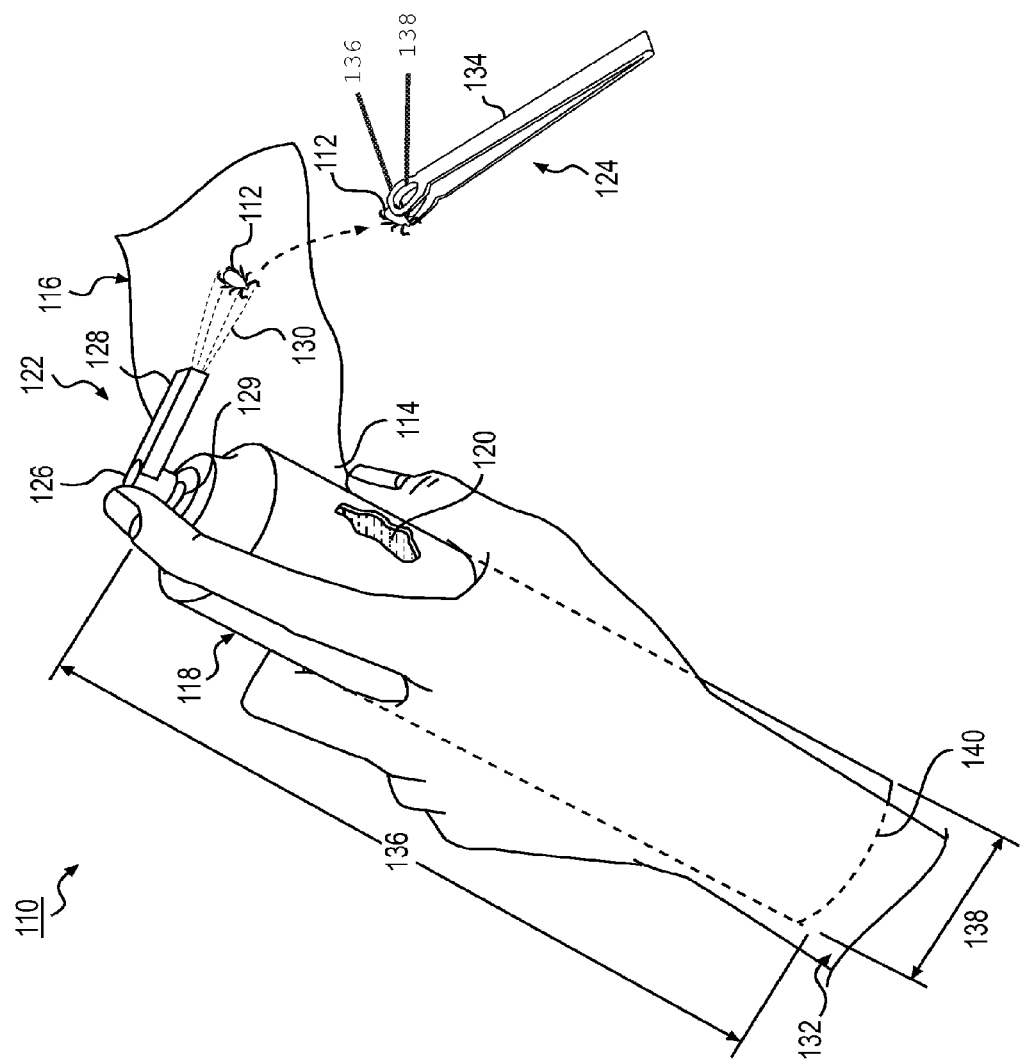

APPARATUS FOR KILLING AND REMOVING TICKS

CROSS-REFERENCE TO RELATED APPLICATION

This application claims the benefit of Provisional Patent Application No. 61/394,391, filed on Oct. 19, 2010, in the United States Patent & Trademark Office, the disclosure of which is incorporated herein by reference.

BACKGROUND OF THE INVENTION

1. Field of the Invention

The present invention relates to a tick remover, and more particularly, an apparatus for killing and removing ticks.

The apparatus utilizes a non-toxic spray that facilitates the safe removal of ticks from humans, pets, livestock, and other mammals. The present invention assists in preventing the transmission of infectious diseases, which may occur during the removal of the tick from its host. The spray is designed to immobilize the tick instantly so that it may be removed easily and safely with a pair of tweezers with two loops. The removal not only helps to prevent infections, such as Lyme disease, but also easily removes the tick without skin irritation or injury to the host.

2. Description of the Prior Art

Removing a tick from a human, pet, or other mammal can be a dangerous and painful process. Many people attempt to use home remedies, such as petroleum jelly, nail polish, alcohol, and the like in hopes that the tick will withdrawal from the body. However, these remedies will only disturb the tick as it is feeding and cause the tick to spit saliva back into the host. The tick's saliva is known to carry a variety of infectious diseases, such as Lyme disease. A more efficient removal is needed.

Numerous innovations for pesticides have been provided in the prior art that will be described. Even though these innovations may be suitable for the specific individual purposes to which they address, however, they differ from the present invention.

A FIRST EXAMPLE, U.S. Pat. No. 4,379,168, Issued on Apr. 5, 1983, to Dotolo teaches pesticide compositions which contain D-limonene as an insect-killing ingredient along with surfactants or emulsifiers and water. The pesticide compositions are liquids designed for use as a flexible-purpose pesticide concentrate; a dip to rid small animals of fleas and ticks; a spray to kill fleas and ticks on small animals and in the kennels of small animals; a spray to kill flies on small animals and in the kennels of small animals; and a spray or liquid to rid household areas of cockroaches and other insect pests. The composition is non-toxic, non-polluting, biodegradable, non-irritating to animals other than insect pests.

A SECOND EXAMPLE, U.S. Pat. No. 4,834,967, Issued on May 30, 1989, to Locicero teaches a method for the removal of ticks and leeches from the skin of mammals including man, dogs, cats, sheep and cattle, wherein the tick or leech is directly sprayed with a compressible liquid refrigerant, in aerosol form, in an amount sufficient to freeze, kill and dislodge the tick or leech from the skin.

A THIRD EXAMPLE, U.S. Pat. No. 6,808,717, issued on Oct. 26, 2004, to Bale teaches a composition of an aerosol coolant spray for killing and removing ticks from human skin, to be dispensed from a pressurized aerosol spray canister. The aerosol coolant spray composition includes a liquid coolant material for freezing the essential oil, and the cooled essential oil is used for immobilizing and killing the tick on the skin of a human. The aerosol coolant spray composition further includes a diluent material being used as a carrier material for emulsifying the essential oil and the coolant material within the pressurized aerosol spray canister.

A FOURTH EXAMPLE, U.S. Patent Office Publication No. 2007/0092545, published on Apr. 26, 2007, to Bale teaches a composition of an aerosol coolant spray for killing and removing ticks from mammal skin, to be dispensed from a pressurized aerosol spray canister. The aerosol coolant spray composition includes a liquid coolant material for freezing the essential oil and the cooled essential oil for immobilizing and killing the tick on the skin of a mammal. The aerosol coolant spray composition further includes a diluent material being used as a carrier material for emulsifying the essential oil and the coolant material within the pressurized aerosol spray canister.

A FIFTH EXAMPLE, U.S. Patent Office Publication No. 2007/0112379, Published on May 17, 2007, to Vaie teaches a device for the removal of ticks from the skin of humans and animals comprising a forceps configuration for grasping the tick's body in the region of the skin surface, as well as a reservoir having an actuation means for a freeze spray to be sprayed onto the tick's body prior to its removal, provision is made for a main body to be provided that incorporates a hollow space for accommodating the reservoir for the defrosting [sic] spray, a discharge nozzle for the freeze spray on the underside of the main body, and a forceps configuration that extends around the main body into the region below the discharge nozzle.

A SIXTH EXAMPLE, U.S. Patent Office Publication No. 2008/0069785, published on Mar. 20, 2008, to Jones teaches pest-combating compositions containing pest-control actives are formulated for sustained pest-combating efficacy, utilizing actives fatty acids, undecanone, and/or soy methyl ester in varying combinations. Pest-combating includes both repellency and killing of pests. In specific formulations, the pest-combating composition includes any one, two or three of the active agents soy methyl ester, fatty acid and undecanone. Fatty acids may be unmodified or may be modified by transesterification or methanolysis of the oleochemical or conversion of the fatty acids to alkyl esters. The composition may be constituted as a spray composition, lotion, paste, or other compositional form. Pests that may be usefully combated with such composition include aphids, ants, bed bugs, bees, beetles, centipedes, caterpillars, chiggers, cockroaches, crickets, cutworms, earwigs, fleas, flies, fire ants, gnats, grasshoppers, hookworms, japanese beetles, june bugs, lice, locust, maggots, mealworms, mealybugs, millipedes, mites, mosquitoes, moths, pillbugs, scorpions, silverfish, spiders, stinkbugs, termites, thrips, ticks, wasps, and white flies.

A SEVENTH EXAMPLE, U.S. Pat. No. 7,531,186, issued on May 12, 2009, to Boeckh et al. teaches inter alia, novel topical formulations comprising at least one 1-N-arypyrazole derivative and amitraz and to methods for treating, controlling, or preventing parasite infestations on mammals or birds. The inventive formulations include spot-on, pour-on or spray formulations and may include a further ectoparasiticide, such as an IGR compound, an avermectin or milbemycin derivative, or a pyrethroid insecticides, and anthelmintics, such as benzimidazoles and imidazothiazoles. The inventive formulation provides a larger duration of parasite control at a faster rate of control. The inventive formula remains effective up to three months from the first application. Moreover, the inventive formulations prevent tick attachment to the animal, thereby providing protection against tick borne diseases. The ectoparasites which may be controlled, treated or prevented by the present invention includes ticks, fleas, mites, mange, lice, mosquitoes, flies and cattle grubs.

AN EIGHTH EXAMPLE, U.S. Patent Office Publication No. 2010/0227010, published on Sep. 9, 2010, to Jones teaches a pest-combating composition including sodium lauryl sulfate and one or more of C. sub. 6-12 fatty acids, preferably lauric and/or capric and/or caprylic acid, soy methyl ester, and 2-undecanone, and methods of combating pests utilizing same, are disclosed. The compositions can include a carrier oil such as silicon oil, soy methyl ester, or a vegetable oil, and can be in the form of an emulsion. The composition may be constituted as a spray composition, an aerosol, a lotion, a paste, or another compositional form. Pests that may be usefully combated with such composition include flying insects, including flies, mosquitoes, and wasps, ants, including arthropods such as fire ants, ticks, fleas, cockroaches, silver fish, thrips, gnats, aphids, Japanese beetles, and agricultural and horticultural arthropods and insects including beetles (potato and bean), flea beetles, fleahoppers, squash bugs, slugs, leaf hoppers, harlequin bugs, milk weed bugs, spiders, mites, lice, rodents, and deer.

It is apparent now that numerous innovations for pesticides have been provided in the prior art that are adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide an apparatus for killing and removing ticks that avoids the disadvantages of the prior art.

ANOTHER OBJECT of the present invention is to provide an apparatus for killing and removing ticks that is simple and inexpensive to manufacture.

STILL ANOTHER OBJECT of the present invention is to provide an apparatus for killing and removing ticks that is simple to use.

BRIEFLY STATED, STILL YET ANOTHER OBJECT of the present invention is to provide an apparatus for killing and removing ticks from the skin of mammals which comprises an aerosol canister. An environmentally safe refrigerant is carried within the aerosol canister. A mechanism is for dispensing the environmentally safe refrigerant from the aerosol canister directly onto a tick to immobilize and kill the tick. Another mechanism is for safely removing the dead tick from the skin of a mammal.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The FIGURES of the drawings are briefly described as follows:

FIG. 1 is a perspective view showing the present invention in use.

REFERENCE NUMERALS UTILIZED IN THE DRAWING 110 apparatus
112 tick
114 skin of mammal 116
116 mammal
118 aerosol canister of apparatus 110
120 refrigerant (HFO-1234yf) of apparatus 110
122 dispensing mechanism of apparatus 110
124 safely removing mechanism of apparatus 110
126 spray valve of dispensing mechanism 122
128 applicator tube of dispensing mechanism 122
129 top of aerosol canister 118
130 a flared beam of aerosols
132 person
134 pair of tweezers with two loops for safely removing mechanism 124
136 length of aerosol canister 118
138 width of aerosol canister 118
140 bottom base of aerosol canister 118

DETAILED DESCRIPTION OF THE PREFERRED EMBODIMENT

As shown in FIG. 1, the present invention is an apparatus 110 for killing and removing ticks 112 from the skin of mammals 116 which comprises an aerosol canister 118. An environmentally safe refrigerant 120 is carried within the aerosol canister 118. A mechanism 122 is for dispensing the environmentally safe refrigerant 120 from the aerosol canister 118 directly onto a tick 112 to immobilize and kill the tick 112. Another mechanism 124 is for safely removing the dead tick 112 from the skin 114 of a mammal 116.

The environmentally safe refrigerant 120 comprises HFO-1234yf that instantly kills the tick 112 by lowering the body temperature of the tick 112 to below thirty two degrees Fahrenheit. The 2,3,3,3-Tetrafluoropropene, or HFO-1234yf, is a fluorinated hydrocarbon with the formula $CH_2=CFCF_3$. It has been proposed as a replacement for R-134a as a refrigerant in automobile air conditioners. The HFO-1234yf is the first in a new class of refrigerants developed to have almost no environmental impact, acquiring a global warming potential (GWP) rating 335 times less than that of R-134a and an atmospheric lifetime of about 400 times shorter.

The dispensing mechanism 122 comprises a non-continuous spray valve 126 on the aerosol canister 118. An applicator tube 128 extends from the top 129 of the aerosol canister 118. When a flared beam of aerosols 130 is placed against the tick 112 on the skin 114, the spray valve 126 will be manually pressed by a person 132 to precisely release a specific amount of the refrigerant 120 in the flared beam of aerosols and onto the tick 112 to kill the tick 112.

The safely removing mechanism 124 comprises a pair of tweezers 134 with two loops 136 that define two openings 138 extending completely through the pair of tweezers 134 in a direction transverse to a longitudinal axis of the pair of tweezers and in which the person 132 will manually remove the dead tick 112 from the skin 114 of the mammal 116. The tweezers 134 can be made of metal or plastic. The aerosol canister 118 measures approximately four and nine sixteenth inches in length, as indicated with numeral 136; by one inch in width, as indicated with numeral 138 across the bottom base 140. The canister 118 can be made of metal or plastic.

In review, the apparatus 110 utilizes a spray that assists in the safe and easy removal of ticks 112 from both humans and animals. The present invention is comprised of an aerosol canister 118 which measures approximately four and nine sixteenth inches in length, as indicated with numeral 136; by one inch in width, as indicated with numeral 138 across the bottom base 140. The aerosol canister 118 contains an environmentally safe refrigerant 120 that instantly kills the tick 112 by lowering the body temperature of the tick 112 to below thirty two degrees Fahrenheit. The refrigerant 120 used is HFO-1234yf. The aerosol canister 118 includes an applicator tube 128 and a specially designed valve 126, which has a non-continuous spray. A flared beam of aerosols 130 is placed on the tick 112 and the spray valve 126 is pressed. The spray valve 126 precisely measures the amount of refrigerant 120 to be dispensed such as two to four milligrams of refrigerant in each spray. The spray makes precisely contact with the tick 112 only and the flow of the refrigerant 120 is halted automatically. The tick 112 is immobilized and can then be easily removed with a pair of tweezers 134 with two loops. The person 132 can provide a number of applications. The tweezers 134 can be made of metal or plastic. When the aerosol canister 118 is empty, it may be discarded. The canister 118 can be made of metal or plastic. The spray leaves behind no residue on the skin 114 and will not seep into the skin 114. The exact specifications may vary.

It will be understood that each of the elements described above, or two or more together, may also find a useful application in other types of constructions differing from the types described above.

While the invention has been illustrated and described as embodiments of an apparatus for killing and removing ticks, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An apparatus for killing and removing ticks from the skin of mammals which comprises:
   a) an aerosol canister;
   b) a fluorinated hydrocarbon environmentally safe refrigerant carried within the aerosol canister, the fluorinated hydrocarbon environmentally safe refrigerant comprising 2,3,3,3-Tetrafluoropropene, which is a fluorinated hydrocarbon with the formula $CH_2=CFCF_3$ that instantly kills the tick by lowering the body temperature of the tick to below thirty two degrees Fahrenheit;
   c) means for dispensing the environmentally safe refrigerant from the aerosol canister directly onto a tick to immobilize and kill the tick;
   d) means for safely removing the dead tick from the skin of a mammal comprising a pair of tweezers with two loops at respective ends thereof in which a person will manually remove the dead tick form the skin of the mammal, the two loops defining two openings that extend completely through the pair of tweezers in a direction which is transverse with respect to a longitudinal axis of the pair of tweezers, and
   e) wherein the dispensed refrigerant makes contact with the tick only and the flow of the refrigerant is halted automatically.

2. The apparatus as recited in claim 1, wherein the dispensing means comprises:
   a) a non-continuous spray valve on the top of aerosol canister; and
   b) an applicator tube extending from the top of the aerosol canister, whereby when a flared beam of aerosols is placed against the tick on the skin, the spray valve will be manually pressed by a person to precisely release a specific amount of the refrigerant in the flared beam of aerosols onto the tick to kill the tick.

3. The apparatus as recited in claim 1, wherein the tweezers can be made of metal.

4. The apparatus as recited in claim 1, wherein the tweezers can be made of plastic.

5. The apparatus as recited in claim 1, wherein the aerosol canister measures approximately four and nine sixteenth inches in length by one inch in width across a bottom base.

6. The apparatus as recited in claim 5, wherein the canister be made of metal.

7. The apparatus as recited in claim 5, wherein the canister can be made of plastic.

* * * * *